United States Patent
Inoue (10) Patent No.: US 9,554,894 B2
(45) Date of Patent: Jan. 31, 2017

(54) INTRAOCULAR LENS INSERTION DEVICE AND CARTRIDGE

(75) Inventor: Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 392 days.

(21) Appl. No.: 12/995,263

(22) PCT Filed: Jun. 3, 2009

(86) PCT No.: PCT/JP2009/060184
§ 371 (c)(1),
(2), (4) Date: Dec. 15, 2010

(87) PCT Pub. No.: WO2009/148091
PCT Pub. Date: Dec. 10, 2009

(65) Prior Publication Data
US 2011/0082463 A1 Apr. 7, 2011

(30) Foreign Application Priority Data
Jun. 5, 2008 (JP) .................................. 2008-147781

(51) Int. Cl.
*A61F 2/16* (2006.01)
(52) U.S. Cl.
CPC ............ *A61F 2/1664* (2013.01); *A61F 2/1691* (2013.01)
(58) Field of Classification Search
CPC ........................... A61F 2/1664; A61F 2/1691
USPC ......................................... 606/107; 623/6.12
See application file for complete search history.

(56) References Cited

U.S. PATENT DOCUMENTS

| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |

(Continued)

FOREIGN PATENT DOCUMENTS

| DE | 3610925 | 10/1987 |
| DE | 4110278 | 10/1992 |

(Continued)

OTHER PUBLICATIONS

International Search Report dated Jul. 7, 2009 for PCT App. Ser. No. PCT/JP2009/060184.

(Continued)

*Primary Examiner* — Gregory Anderson
*Assistant Examiner* — Sarah Simpson
(74) *Attorney, Agent, or Firm* — Henricks, Slavin & Holmes LLP (57) ABSTRACT

An intraocular lens insertion device and a cartridge which enable the intraocular lens to be inserted into an eye more stably and easily than ever before. A supporting portion 102 of an intraocular lens 100 arranged on a lens-advancing side in a lens-advancing direction x is pressed against a protrusion 21 so as to be bent backward. Thus, releasing the intraocular lens 100 from a nozzle portion 13 is allowed to begin with the releasing of a curved portion of the supporting portion 102 that has become U-shaped and hard to move freely. As a result, there can be provided an intraocular lens insertion device and a cartridge which enable the intraocular lens 100 to be inserted into an eye more steadily and easily than ever before.

10 Claims, 8 Drawing Sheets

(56) References Cited

U.S. PATENT DOCUMENTS

| | | |
|---|---|---|
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 * | 8/2003 | Blake ............... A61F 2/1664 606/107 |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |

(56) References Cited

U.S. PATENT DOCUMENTS

| | | |
|---|---|---|
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 * | 9/2013 | Ichinohe et al. .............. 606/107 |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0200167 A1 * | 9/2006 | Peterson ............... A61F 2/1678 606/107 |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 * | 1/2007 | Makker et al. .............. 623/6.12 |
| 2008/0033449 A1 * | 2/2008 | Cole et al. .................... 606/107 |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 * | 8/2009 | Ichinohe et al. .............. 606/107 |
| 2009/0216244 A1 | 8/2009 | Pynson |
| 2009/0248031 A1 | 10/2009 | Ichinohe |
| 2010/0106160 A1 | 4/2010 | Tsai |
| 2010/0161049 A1 | 6/2010 | Inoue |
| 2010/0185206 A1 | 7/2010 | Ichinohe |
| 2010/0217273 A1 | 8/2010 | Someya et al. |
| 2010/0286704 A1 | 11/2010 | Ichinohe |
| 2010/0331808 A1 | 12/2010 | Py et al. |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2016/0193038 A1 | 7/2016 | Kudo et al. |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |

(56) References Cited

FOREIGN PATENT DOCUMENTS

| | | |
|---|---|---|
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO 2005/084588 A1 | 9/2005 |
| WO | WO2006070628 A1 | 7/2006 |
| WO | WO 2006/090531 A1 | 8/2006 |
| WO | WO2006080191 A1 | 8/2006 |
| WO | WO2007037223 A1 | 4/2007 |
| WO | WO2007097221 A1 | 4/2007 |
| WO | WO 2007/080869 A1 | 7/2007 |
| WO | WO 2008/149794 A1 | 12/2008 |
| WO | WO2008149795 A1 | 12/2008 |
| WO | WO2009058929 A1 | 7/2009 |
| WO | WO 2009/148091 A1 | 12/2009 |
| WO | WO2011126144 A1 | 10/2011 |
| WO | WO2011155636 A1 | 12/2011 |

OTHER PUBLICATIONS

International Preliminary Examination Report dated Jan. 11, 2011 for PCT App. Ser. No. PCT/JP2009/060184.
U.S. Appl. No. 14/145,846, filed Dec. 31, 2013.
U.S. Appl. No. 14/099,989, filed Dec. 8, 2013.
U.S. Appl. No. 14/033,888, filed Sep. 23, 2013.
U.S. Appl. No. 14/011,018, filed Aug. 27, 2013.
U.S. Appl. No. 14/065,365, filed Oct. 28, 2013.
U.S. Appl. No. 15/063,395, filed Mar. 7, 2016.
U.S. Appl. No. 14/812,104, filed Jul. 29, 2015.
U.S. Appl. No. 15/071,880, filed Mar. 16, 2016.

* cited by examiner

INTRAOCULAR LENS INSERTION DEVICE AND CARTRIDGE

TECHNICAL FIELD

This invention relates to an intraocular lens insertion device and a cartridge thereof that are used when implanting an intraocular lens into an aphakic eye after a cataract operation.

BACKGROUND ART

In a cataract operation, removing an opacified lens by phacoemulsification (PEA), and implanting an intraocular lens after removing an opacified lens are widely performed. Intraocular lenses include: a hard intraocular lens whose optical portion is made of a hard material such as PMMA (polymethylmethacrylate), and a soft intraocular lens which is made of a soft material such as silicone elastomer, soft acrylic, or hydrogel.

When using a hard intraocular lens, the intraocular lens must be inserted through an incision formed in the cornea or sclera that is of the same or slightly wider width than the diameter of the optical portion. On the other hand, when using a soft intraocular lens, folding of the optical portion allows the intraocular lens to be inserted into the eye through an incision smaller than the diameter of the optical portion.

Figure 12A:
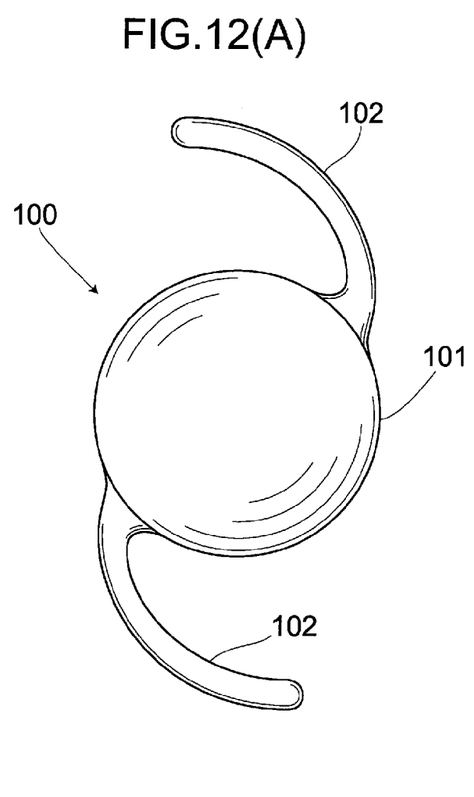
FIG. 12 is a schematic view showing the front and side views of the intraocular lens.
Figure 12B:
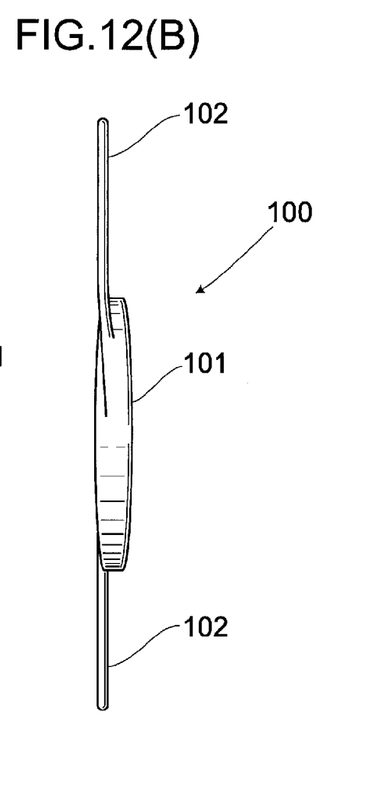

FIG. 12 shows a soft intraocular lens of this kind. A front view is shown in FIG. 12(A) and a side view is shown in FIG. 12(B). In practice, a soft intraocular lens 100 of this kind is formed in a flat circular shape and comprises an optical portion 101 serving as a crystalline lens in an eyeball and two supporting portions 102, 102 formed in a linear shape. These two supporting portions 102, 102 are provided at two symmetrically opposite sections on the circumference of the optical portion 101. The supporting portions 102, 102 are extended in the form of a circular arc in such a manner as gradually departing away from the outer fringe of the optical portion 101 at a curvature slightly larger than that of the outer fringe of the optical portion 101.

The soft intraocular lens 100 of this kind is designed so as to be able to be inserted through a small incision into an eye after the optical portion 101 thereof is folded in two by an intraocular lens insertion device disclosed, for example, in Intl Application Publication Pamphlet of WO2006/090531 or Japanese Unexamined Patent Application Publication No. 2004-351196.

Patent Document 1: WO2006/090531 Intl Application Publication Pamphlet
Patent Document 2: Japanese Unexamined Patent Application Publication No. 2004-351196

DISCLOSURE OF THE INVENTION

Problems to be Solved by the Invention

Figure 13:
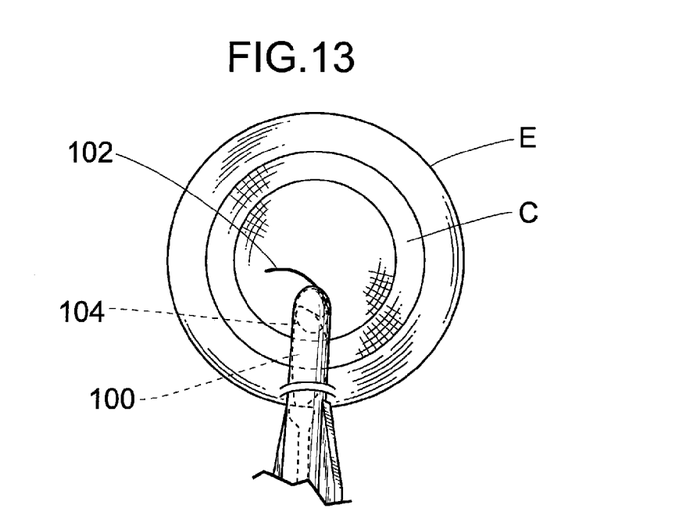
FIG. 13 is a schematic view illustrating how the intraocular lens is inserted into the eye using the intraocular lens insertion device.

According to these conventional intraocular insertion devices, however, there is a problem that proficiency is required to insert the intraocular lens 100 into the eye while keeping the distal end of the supporting portion 102 stable because when inserting the intraocular lens 100 into a lens capsule C inside an eyeball E, the distal end of the supporting portion 102 is foremost discharged from a discharge port 104, as shown in FIG. 13, and thus the distal end of the supporting portion 102 is prone to be moved freely.

In view of the problem described above, it is, therefore, an object of the present invention to provide an intraocular lens insertion device and cartridge thereof which enable an intraocular lens to be inserted into an eye more easily and more stably as compared to by the conventional ones.

Means for Solving the Problem

In order to achieve the object of the present invention, the present invention according to a first aspect is characterized by an intraocular lens insertion device comprising:

an cylindrical insertion portion to place therein an intraocular lens having one or more supporting portions provided on an outer fringe of an optical portion thereof, said intraocular lens insertion device pushing out said intraocular lens by a plunger, and then releasing said intraocular lens to an outside from a nozzle portion of said cylindrical insertion portion, wherein said supporting portion arranged on an advancing side with respect to a lens-advancing direction is bent backward by a bending means in said cylindrical insertion portion.

The present invention according to a second aspect is characterized in that said bending means is a protrusion while said supporting portion is pressed against said protrusion to be bent backward.

The present invention according to a third aspect is characterized in that said protrusion is detachably provided in said cylindrical insertion portion.

The present invention according to a fourth aspect is characterized in that said protrusion is provided in a separate casing while said casing is detachably attached to said cylindrical insertion portion.

The present invention according to a fifth aspect is characterized in that said plunger is provided in a main body of the insertion device, while said cylindrical insertion portion is a cartridge attached to said main body of the insertion device, wherein said cartridge is separated from said casing and attached to said main body of the insertion device after said supporting portion of the intraocular lens placed on a lens placement portion is bent by said protrusion.

The present invention according to a sixth aspect is characterized in that said intraocular lens is of a preset type with said intraocular lens set in advance.

The present invention according to a seventh aspect is characterized by a cartridge attached to a main body of an insertion device provided with a plunger for pushing out an intraocular lens having one or more supporting portions provided on an outer fringe of an optical portion thereof, comprising:

a lens placement portion to place therein said intraocular lens from a lens insertion opening;

a nozzle portion communicating with said lens placement portion to release said intraocular lens to an outside, wherein said supporting portion arranged on an advancing side with respect to a lens-advancing direction is bent backward by a bending means in said lens placement portion.

The present invention according to an eighth aspect is characterized in that said bending means is a protrusion while said supporting portion is pressed against said protrusion to be bent backward.

The present invention according to a ninth aspect is characterized in that said protrusion is detachably provided in said lens placement portion.

The present invention according to a tenth aspect is characterized in that said protrusion is provided in a separate casing while said casing is detachably attached to said lens placement portion.

The present invention according to an eleventh aspect is characterized in that said cartridge is separated from said casing and attached to said main body of the insertion device after said supporting portion of the intraocular lens placed on said lens placement portion is bent by said protrusion.

Effects of the Invention

In accordance with the intraocular lens insertion device according to the first aspect and the cartridge according to the seventh aspect, the supporting portion of the intraocular lens placed on the lens advancing side is bent backward by the bending means, thus enabling the intraocular lens to be released after it is folded and made less likely to move freely when it is released from the nozzle. Thus, the intraocular lens can be more easily inserted into an eye with the same kept in a more stable condition than by the conventional ones.

In accordance with the intraocular lens insertion device according to the third aspect and the cartridge according to the ninth aspect, it is possible to prevent the protrusion from blocking the movement when inserting the intraocular lens into an eye.

In accordance with the intraocular lens insertion device according to the fourth aspect and the cartridge according to the tenth aspect, the protrusion is provided in the casing, and thus even thin and short protrusion can be easily engaged or disengaged by just attaching or detaching the casing to or from the cartridge.

In accordance with the intraocular lens insertion device according to the sixth aspect, in a preset type in which a lens is set in advance, the intraocular lens can be released after it is folded and made less likely to move freely when it is released from the nozzle. Thus, the intraocular lens can be more easily inserted into an eye with the same kept in a more stable condition than by the conventional ones.

BEST MODE FOR CARRYING OUT THE INVENTION

Preferred embodiments of the present invention are described hereinafter with reference to the drawings.

First Embodiment (1) Basic Structure of Intraocular Lens Insertion Device

Figure 1:
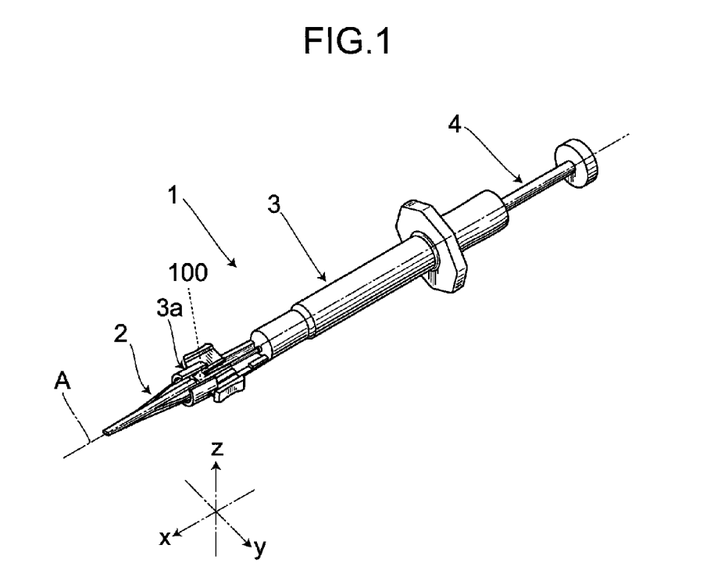
FIG. 1 is a schematic view showing the whole structure of an intraocular lens insertion device according to a first embodiment of the invention.

In FIG. 1, reference numeral 1 indicates an intraocular lens insertion device as a whole. The intraocular lens insertion device 1 comprises a cartridge 2 and an insertion device body 3 having a plunger 4. The cartridge 2 is attached to an attaching portion 3a of the insertion device body 3. Further, the intraocular lens insertion device 1 has an intraocular lens 100 installed in the cartridge 2, and is structured so as to be able to discharge the intraocular lens 100 from the tip end of the cartridge 2 into an eye by pushing out the intraocular lens 100 in the lens-advancing direction x (i.e., the direction of an arrow x, or an anterior direction in the lens-advancing axis A) using the plunger 4.

(2) Structure of Cartridge

Figure 2A:
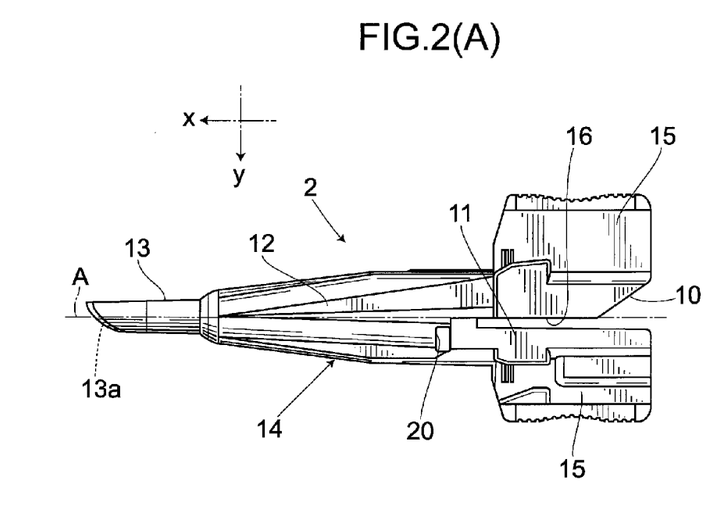
FIG. 2 is a schematic view showing the front and side views of a cartridge.

The cartridge 2 attached to the insertion device body 3 as referred to above is described further below. As shown in FIG. 2 (A), the cartridge 2, serving as a cylindrical or tubular insertion portion, comprises a cartridge body 14 composed of a lens insertion opening 10, a lens placement portion 11, a transition portion 12 and a nozzle 13 in sequence, along the lens-advancing axis A; and wings 15, 15 extending from both side faces of the cartridge body 14 along the lateral direction y perpendicular to the lens-advancing direction x.

The lens insertion opening 10 is provided with an insertion groove 16 formed on upper and lower surfaces by being cut out in the lens-advancing direction x. The lens placement portion 11 is provided anterior to the lens insertion opening 10 with respect to the lens-advancing axis A, and the transition portion 12 is provided anterior to the lens placement portion 11 with respect to the lens-advancing axis A. An inner wall of the transition portion 12 is formed in the shape of a mortar gradually tapering toward the tip end thereof, and the tip end of the transition portion 12 is communicated with the nozzle 13.

In this way, the cartridge body 14 is formed such that the intraocular lens 100 can be moved from the lens placement portion 11 through the transition portion 12 to the nozzle 13 in sequence by being pushed with the plunger 4 in the lens-advancing direction x. Also, the cartridge body 14 is formed so as to be able to discharge the intraocular lens pushed by the plunger 4 into the eye from a discharge port 13a of the nozzle 13. Here, the nozzle 13 is contoured so that it can be inserted into an incision (not shown).

Figure 2B:
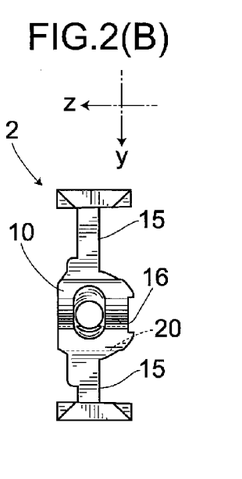
Figure 3:
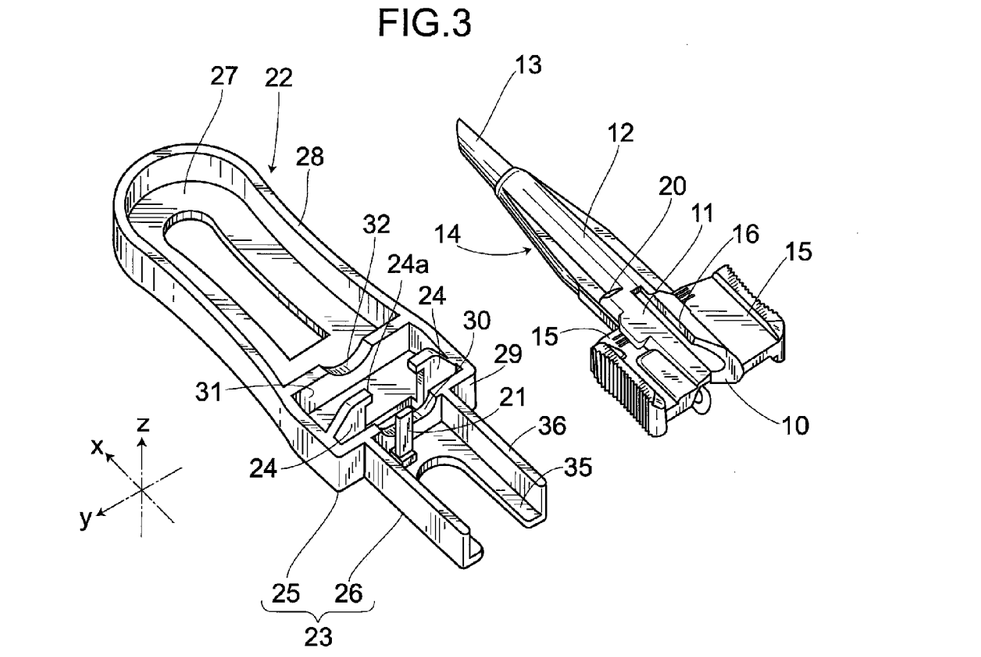
FIG. 3 is a perspective view showing the whole structure of the cartridge and a casing.

In addition to the above-mentioned basic structure, the cartridge 2 of the present invention is provided with a protrusion insertion hole 20 formed so as to penetrate the thickness thereof in the vicinity of the lens placement portion 11 toward the vertical direction z perpendicular to both the lens-advancing direction x and the lateral direction y, as illustrated in FIGS. 2(A) and 2(B). In the case of the present embodiment, the protrusion insertion hole 20 is, as shown in FIG. 2(A), shifted toward one side relative to the lens-advancing axis A (in this case, downward) and is formed so as to allow a hole region thereof to cross only a part of a transition space in which the intraocular lens 100 moves.

Furthermore, the cartridge 2 is formed so as to be detachable from a casing 22 on which a protrusion 21 is vertically provided so that the protrusion 21 may be inserted into the protrusion insertion hole 20 by attaching the cartridge 2 to the casing. When the cartridge 2 is attached to the casing 22 and thus the protrusion 21 is inserted into the protrusion insertion hole 20, the protrusion 21 is allowed to pass through a part of the transition space in the cartridge 2 so that the tip end of the protrusion 21 is exposed to the outside.

Figure 5A:
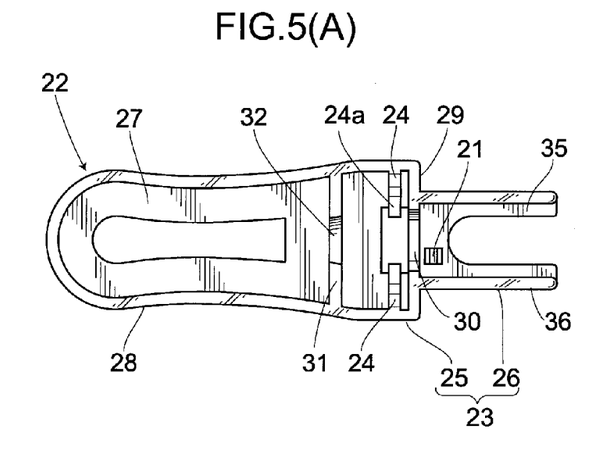
FIG. 5 is a schematic view showing the front, side and back views of the casing.
Figure 5B:
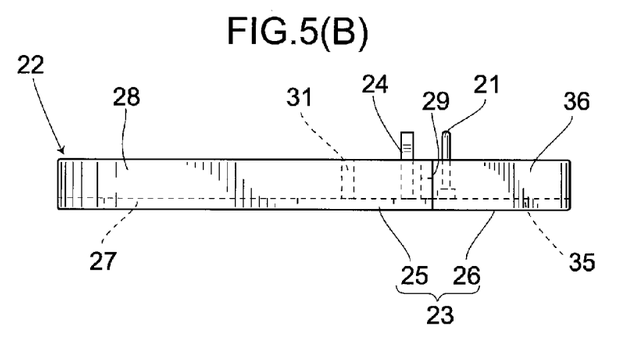
Figure 5C:
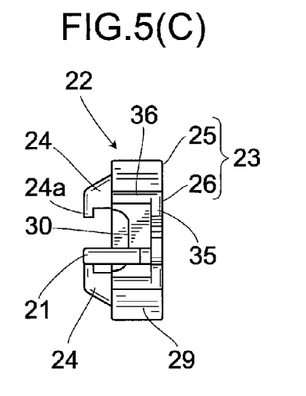

Here, as shown in FIGS. 5(A), 5(B) and 5(C), the casing 22 includes a casing main body 23 to which the cartridge 2 is attached, and the casing main body 23 is provided with fixing claws 24, 24 for fixedly attaching the cartridge 2 to the casing main body 23 and the said protrusion 21 that is to be inserted into the protrusion insertion hole 20 at the time of the attachment of the cartridge 2.

The casing main body 23 is integrally formed of a synthetic resin material such as a plastic material, and comprises a tip-side holding portion 25 holding the transition portion 12 and nozzle 13 of the cartridge 2; and an insertion-side holding portion 26 holding the lens insertion opening 10, lens placement portion 11 and wings 15, 15 of the cartridge 2.

According to the present embodiment, the tip-side holding portion 25 includes a base plate 27 having a bell shape as a whole such that its side faces are slightly concavely curved toward the inside at their central portions, and a wall portion 28 vertically provided along the outer fringe of the base plate 27. Thus, the tip-side holding portion 25 is formed such that the side faces of the wall portion 28 are also slightly concavely curved toward the inside at their central portions, corresponding to the contour of the base plate 27, so that it may be easily held between user's thumb and index finger.

The tip-side holding portion 25 includes a cutout portion 30 provided at a wall portion 29 on a proximal portion thereof adjacent to the insertion-side holding portion 26. The cutout portion 30 is formed by being cut out in a concavely curved manner, corresponding to the contour of the transition portion 12 of the cartridge 2, thereby enabling the transition portion 12 of the cartridge 2 to be placed on the cutout portion 30.

Further, the tip-side holding portion 25 includes an inner wall portion 31 spaced a distance away from the wall portion 29 on the proximal portion, extending toward the lateral direction y. The inner wall portion 31 is cut out in a concavely curved manner, corresponding to the contour of the transition portion 12 of the cartridge 2, thereby enabling the transition portion 12 of the cartridge 2 to be placed on a cutout portion 32 thereof as well.

Furthermore, the tip-side holding portion 25 includes the two fixing claws 24, 24 opposed to each other, at given positions on the base plate 27 between the wall portion 29 on the proximal side and the inner wall portion 31. Here, the two fixing claws 24, 24 have elastic retention capacity as a result of selecting a synthetic resin material as a material, thereby expanding the fixing claws 24, 24 toward the lateral direction y by an external force applied at the time when the cartridge 2 is placed on the casing 22 and returning the fixing claws 24, 24 to an original state at the time when the external force is no longer applied.

The fixing claws 24, 24 are each provided, at their tip end, with an engaging claw 24a folded back toward the upper face side of the cartridge 2, so that the cartridge 2 may be fitted and held in the casing 22 through the two fixing claws 24, 24 of the tip-side holding portion 25.

Figure 4:
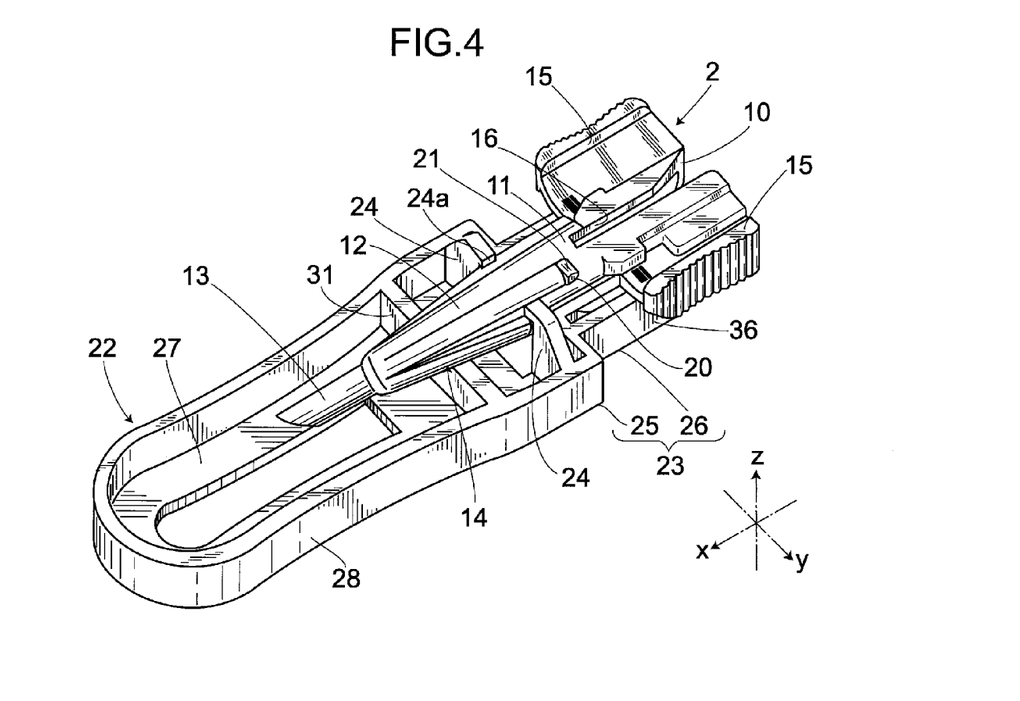
FIG. 4 is a schematic view showing the cartridge being placed onto the casing.

On the other hand, the insertion-side holding portion 26 comprises a base plate 35 formed by cutting a rectangular plate in a letter U shape, and a wall portion 36 vertically provided at both side faces of the base plate 35. The insertion-side holding portion 26 is configured to hold the cartridge 2 due to the wings 15 of the cartridge 2 abutting onto the upper faces of the wall portions 36 when the cartridge 2 is fitted in the fixing claws 24 of the tip-side holding portion 25 (See FIG. 4).

In addition to the above-mentioned structure, the casing 22 of the present invention is provided with the protrusion 21 vertically extending from the base plate 35 of the insertion-side holding portion 26. The protrusion 21 is formed so that it may be able to be inserted into the protrusion insertion hole 20 of the cartridge 2 when the cartridge 2 is installed in the casing 22 through the fixing claws 24, 24 of the tip-side holding portion 25.

In practice, the protrusion 21, serving as a folding means, is strip-shaped and formed to have a given thickness, corresponding to the shape of the opening of the protrusion insertion hole 20 of the cartridge 2, and is vertically provided on the base plate 35 of the insertion-side holding portion 26 so as to be extended in the vertical direction z. With the cartridge 2 being installed on such casing 22, the intraocular lens 100 can be inserted from the lens insertion opening 10 of the cartridge 2.

Figure 6A:
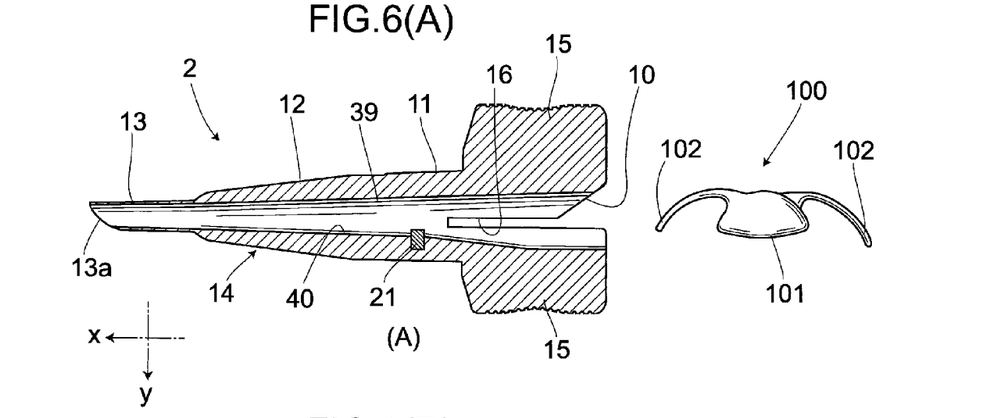
FIG. 6 is a cross-sectional view of the cartridge used for explanation of how the intraocular lens is installed in the cartridge placed onto the casing.
Figure 6B:
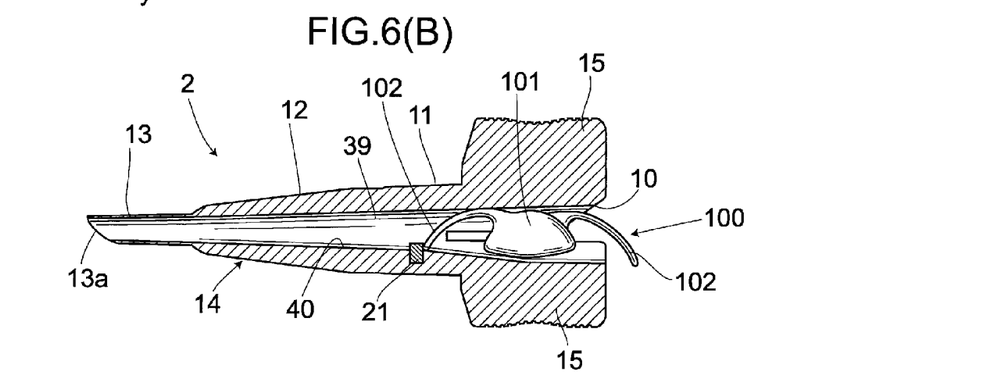

Then, as shown in FIG. 6(A), the optical portion 101 of the intraocular lens 100 is folded in two with supporting portions 102, 102 extended outward. With that posture, the optical portion 101 is grasped with tweezers (not shown), and then, as shown in FIG. 6(B), the intraocular lens is inserted into the lens insertion opening 10 while it is arranged so as to allow the tip end of one of the supporting portions 102 to abut onto the protrusion 21. Here, for sake of simplicity, the casing main body 23 is not shown but only the protrusion 21 is shown in FIG. 6.

Figure 6C:
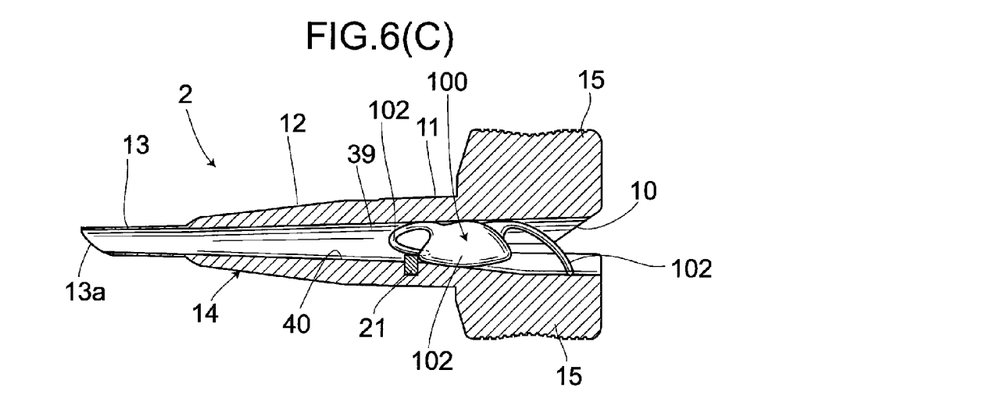

Then, the cartridge 2 allows the distal end of the supporting portion 102 of the intraocular lens 100 to abut onto the protrusion 21 that is exposed within the transition space 39. With the tip actually being abutted onto the protrusion 21, the 25 intraocular lens 100 is inserted up to the lens placement portion 11 by the tweezers. In this way, as shown in FIG. 6(C), the cartridge 2 allows the distal end of the supporting portion 102 to be folded back by the protrusion 21 in the opposite direction against the lens-advancing direction x (hereinafter, this is called backward direction). In other words, the protrusion 21 performs the function of contacting and bending the first supporting portion 102 in the backward direction.

Thus, the cartridge 2 is able to place the intraocular lens 100 on the lens placement portion 11 with the supporting portion 102 being folded in a substantially U-shape by the protrusion 21.

Moreover, the cartridge 2 is formed such that the optical portion 101 of the intraocular lens 100 abuts on the protrusion 21 that is inserted through the protrusion insertion hole 20 and is exposed to the transition space 39, so that the protrusion 21 receives the optical portion 101, thereby precisely positioning the intraocular lens 100 on the lens placement portion 11.

After that, the cartridge 2 is removed from the casing 22 and thus the protrusion 21 is allowed to disengage from the protrusion insertion hole 20. However, the cartridge 2 can keep the distal end of the supporting portion 102 folded back toward the optical portion 101 by allowing the supporting portion 10 of the intraocular lens 100, which had been abutted onto the protrusion 21 until then, to abut onto an inner wall 40 of the transition space 39. In such state, the cartridge 2 is capable of being attached to the attaching portion 3a of the insertion device body 3. Thus, the intraocular lens insertion device 1 allows the intraocular lens 100 to be pushed out by the plunger 4 toward the lens-advancing direction x with the supporting portion 102 being folded back, thus enabling the intraocular lens 100 to be released into an eye from the nozzle 13 provided on the tip end of the cartridge 2.

At this time, the intraocular lens insertion device 1 of the present invention allows the curved portion of the folded supporting portion 102, which has become U-shaped and less likely to move freely, to be exposed from the discharge port 13a of the nozzle 13, and then allows the optical portion 101 to be released from the discharge port 13a thereof by pushing out the intraocular lens 100 by the plunger 4, thereby preventing only the distal end of the supporting portion 102 from being released and moved freely in the process of releasing the intraocular lens 100 into the eye from the tip end of the cartridge 2.

3. Behavior and Effects

According to the above-mentioned structure, the cartridge 2 is installed in the casing 22, thereby allowing the protrusion 21 provided on the casing 22 to be inserted into the protrusion insertion hole 20 so that the protrusion 21 can be exposed to the transition space 39.

A user may insert the intraocular lens 100 from the lens insertion opening 10 with the cartridge 2 being installed in the casing 22, and place the intraocular lens 100 on the lens placement portion 11. At this time, the user can pinch the wall portion 28 of the casing 22 much larger in size than the wings 15, 15 without directly pinching the wings 15, 15 of the cartridge 2, thereby enabling the cartridge 2 to be easily stabilized. Thus, the user can place the intraocular lens 100 on the lens placement portion 11 more easily than by the conventional ones.

Further, the user can hold the cartridge 2 in a stable condition by pinching the wall portion 28 of the casing 22, thus enabling the user to easily fill a viscoelastic material such as a hyaluronic acid preparation for ophthalmic application into the inside of the cartridge 2.

Furthermore, according to the cartridge 2, when the intraocular lens 100 is gradually inserted from the lens insertion opening 10 in order to place the intraocular lens 100 on the lens placement portion 11, the distal end of the supporting portion 102 of the intraocular lens 100 is allowed to abut on the protrusion 21, and thus the distal end of the supporting portion 102 in the lens-advancing direction x can be folded backward.

Particularly, according to the present embodiment, since the protrusion 21 is not exposed all through the transition space 39, but is only exposed in a part thereof at one side in the lens-advancing axis A, it is possible to allow only the distal end of the supporting portion 102 to abut on the protrusion 21, thereby ensuring an intermediate portion between the distal end of the supporting portion 102 and the proximal portion thereof to be folded in a U-shape.

According to the intraocular lens insertion device 1, therefore, the supporting portion 102 of the intraocular lens placed on the lens advancing side with respect to the lens-advancing direction x is pressed against the protrusion 21 to thereby be folded backward, thus enabling the curved portion of the folded supporting portion 102, which has become U-shaped and less likely to move freely, to be first released when releasing the intraocular lens 100 from the nozzle 13. Thus, the intraocular lens 100 can be more easily inserted into an eye with the same kept in a more stable condition than by the conventional ones.

Moreover, the intraocular lens insertion device 1 is detachably provided with the protrusion 21, thereby preventing the protrusion 21 from blocking the movement of the intraocular lens 100 when inserting the intraocular lens 100 into an eye.

Additionally, according to the present embodiment, the protrusion insertion hole 20 of the cartridge 2 is drilled at the top face of the lens placement portion 11 so that the tip of the protrusion 21 of the casing 22 is exposed from the top face of the lens placement portion 11, and thus a user can visually confirm the position of the protrusion 21 in a moment. Accordingly, it is possible to ensure the distal end of the supporting portion 102 to be properly placed on the side of the protrusion 21 so that the supporting portion 102 may be pressed to the protrusion 21 and folded when the intraocular lens 100 is placed on the lens placement portion 11.

Also, according to the present embodiment, the protrusion 21 is provided on the casing 22, and thus even thin and short protrusion 21 can be inserted into and removed from the protrusion insertion hole 20 of the cartridge 2 by just attaching and detaching the casing 22 to and from the cartridge 2.

Besides, the cartridge 2 is installed in the casing 22, and thus the nozzle 13, the transition portion 12 and the like can be protected against an external force owing to the casing 22. In addition, the cartridge 2 can be placed on a pedestal with the casing 22 installed, thus preventing the nozzle 13, the transition portion 12 and the like from directly contacting the pedestal. Accordingly, the cartridge 2 can be always kept clean.

Second Embodiment

FIG. 7 which is given the same reference numerals as corresponding parts in FIG. 6 shows a cartridge according to a second embodiment. A cartridge 50 is different from that of the foregoing first embodiment in that the optical portion 101 is inserted into a lens insertion opening 51 without being folded in half.

Figure 7A:
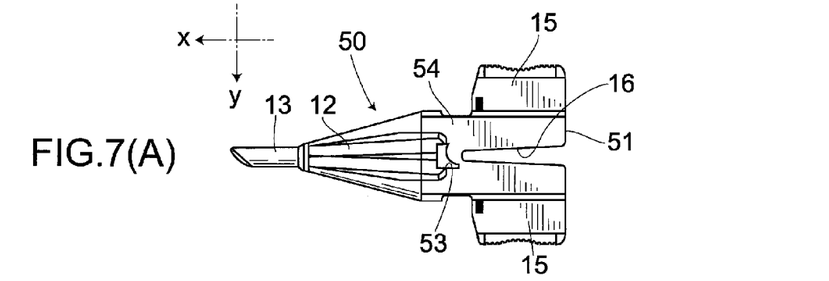
FIG. 7 is a cross-sectional view of the cartridge used for explanation of how the intraocular lens is installed in the cartridge according to a second embodiment.
Figure 7B:
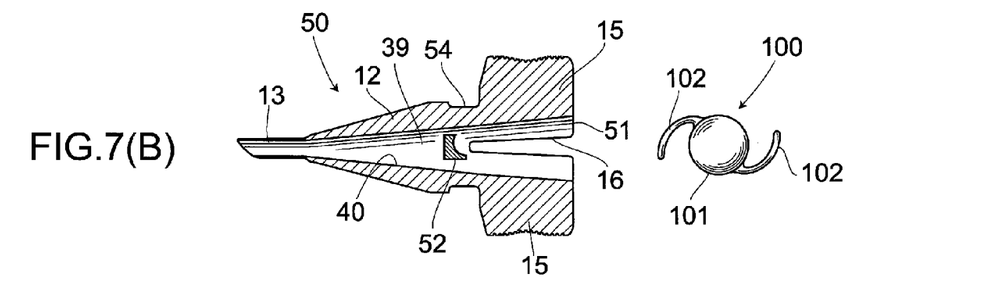

In practice, as shown in FIGS. 7(A) and 7(B), the cartridge 50 is formed so as to be able to be installed in the casing not shown in the drawings. When it is installed in the casing, a protrusion 52 provided on the casing is allowed to be inserted into a protrusion insertion hole 53. In the meantime, for sake of simplicity, the casing is not shown in FIG. 7 but only the protrusion 52 is shown therein.

In practice, the protrusion insertion hole 53 is drilled so as to penetrate the thickness in the vicinity of the lens placement portion 54 toward the bottom-to-top direction (toward a viewer seeing the drawing) perpendicular to both the lens-advancing direction x and the lateral direction y. In this embodiment, the protrusion insertion hole 20 is drilled in the substantial center of the lens placement portion 54 so as to cross the lens-advancing axis A, and thus an hole region is formed in the middle of the transition space in which the intraocular lens 100 moves.

Thus, when the protrusion 52 is inserted into protrusion insertion hole 53 by installing the cartridge 50 in the casing, the protrusion 52 passes through the middle of the transition space 39 and the tip of the protrusion 52 can be exposed to the outside.

Figure 7C:
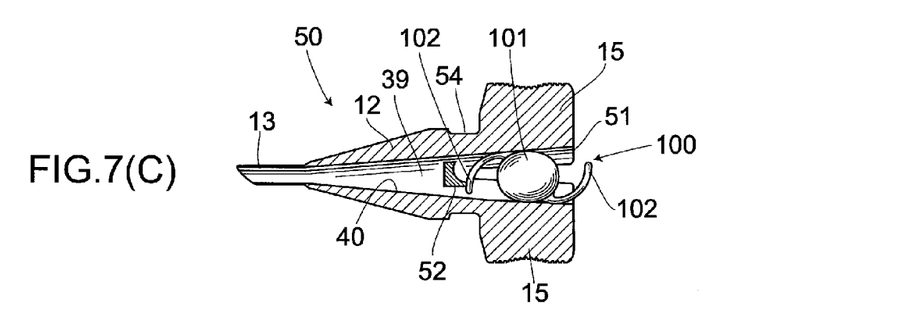
Figure 7D:
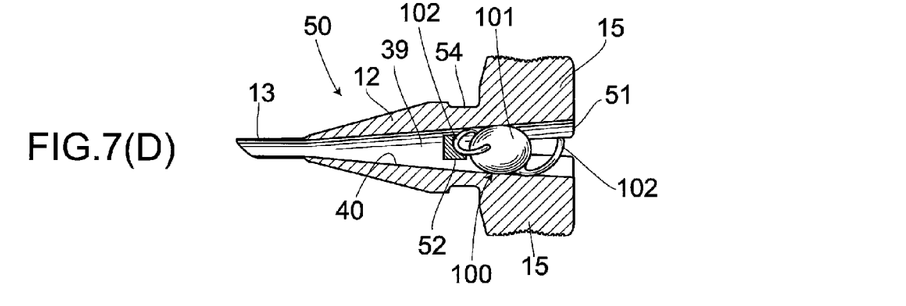

In that state, the intraocular lens 100 is pinched with a tweezers (not shown) with the supporting portions 102, 102 extending outwardly and the optical portion 101 unfolded, and then it may be inserted into the lens insertion opening 51 of the cartridge 50, with the tip of one supporting portion 102 being the leading end, as illustrated in FIG. 7(C).

At this time, the cartridge 50 allows the distal end of the supporting portion 102 of the intraocular lens 100 to abut on the protrusion 21 exposed inside the transition space 39. In that state, the intraocular lens 100 is inserted up to the lens placement portion 54 by the tweezers. In this way, as shown in FIG. 6(D), the cartridge 50 allows the distal end of the supporting portion 102 to be folded back along a curved surface of the protrusion 52 in the opposite direction relative to the lens-advancing direction x. Thus, the cartridge 50 enables the intraocular lens 100 to be placed on the lens placement portion 54 with the supporting portion 102 being folded in a U-shape by the protrusion 52.

In this embodiment, the surface of the protrusion 52 on which the supporting portion 102 of the intraocular lens 100 abuts is curved toward a given direction, thereby ensuring the supporting portion 102 of the intraocular lens 100 to be bent in a desired direction along the curved surface.

After that, like in the above-mentioned first embodiment, the cartridge 50 is removed from the casing and thus the protrusion 52 disengages from the protrusion insertion hole 53. The cartridge 50, however, is capable of keeping the distal end of the supporting portion 102 folded due to the supporting portion 102 of the intraocular lens 100, which had been abutted on the protrusion 52 until then, to then abut onto the inner wall 40 in the transition space 39. In such state, the cartridge 50 is capable of being attached to the attaching portion of the insertion device body not shown. Thus, the intraocular lens insertion device allows the intraocular lens 100 to be pushed out by the plunger 4 in the lens-advancing direction x with the supporting portion 102 being folded back, thus enabling the intraocular lens 100 to be released into an eye from the nozzle 13 provided on the tip end of the cartridge 2.

Third Embodiment

Figure 8:
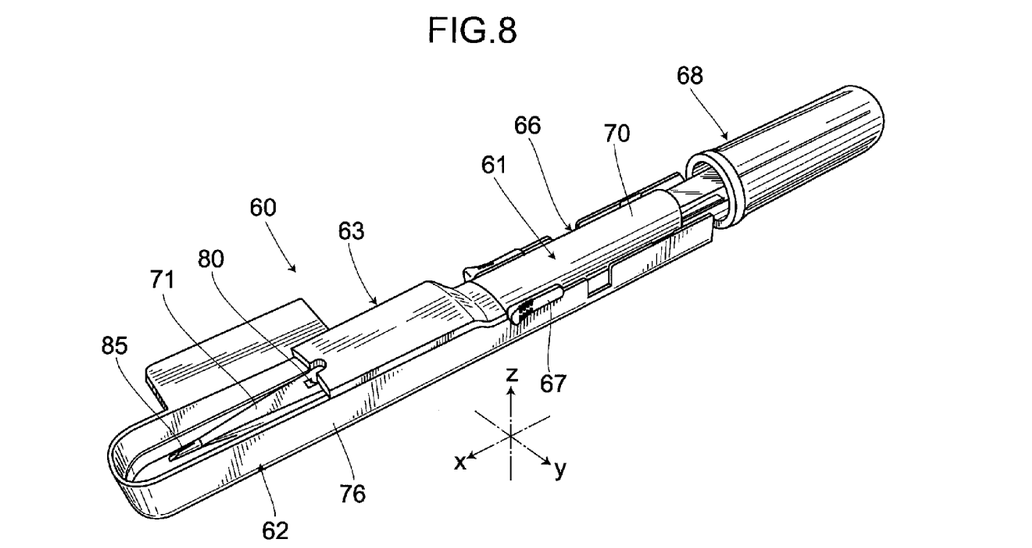
FIG. 8 is a perspective view showing the whole structure of the intraocular lens insertion device with the casing according to a third embodiment.

In FIG. 8, numeral 60 denotes an assembly of an intraocular lens insertion device and a casing according to a third embodiment. The assembly 60 of an intraocular lens insertion device and a casing comprises an intraocular lens insertion device 61, a casing 62 on which the intraocular lens insertion device 61 is detachably installed, and a cover body 63 which is detachably attached to the casing 62 on which the intraocular lens insertion device 61 is installed to cover the intraocular lens insertion device 61.

At first, the intraocular lens insertion device 61 is described hereinbelow. The intraocular lens insertion device 61 is of a preset-type in which the intraocular lens 100 is set in advance, unlike in the foregoing first and second embodiments.

Figure 9:
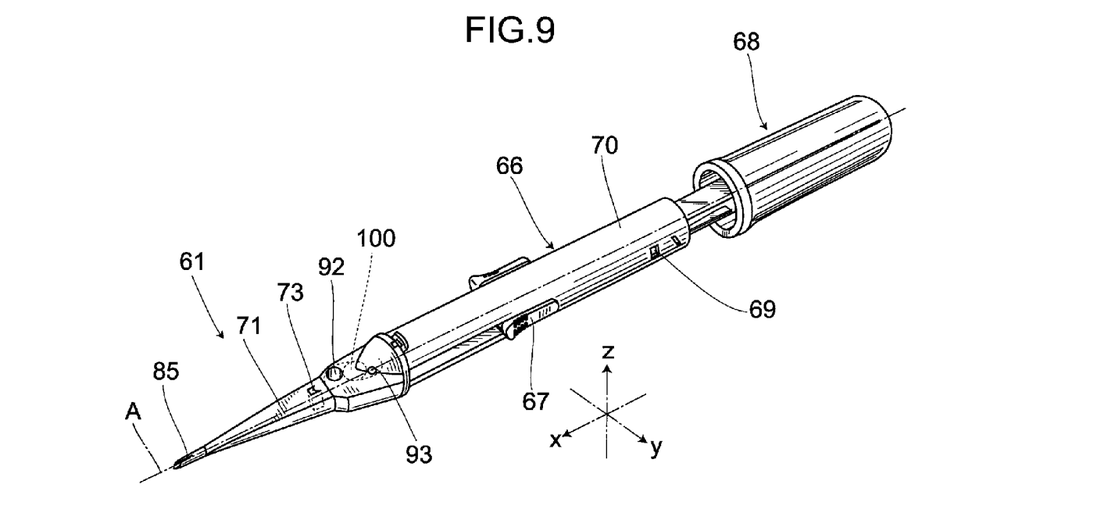
FIG. 9 is a perspective view showing the structure of the intraocular lens insertion device according to the third embodiment.

As shown in FIG. 9, the intraocular lens insertion device 61 comprises a main body 66, a slider 67, a plunger 68 and a locking mechanism, and this main body 66 comprises a cylindrical proximal member 70 and a tapered distal member 71.

In this case, a lens placement portion (not shown) made of a plate member is provided in the distal portion of the proximal member 70 on the lens advancing side with respect to the lens-advancing axis A so that the intraocular lens 100 may be placed on the lens placement portion. Further, the tapered distal member 71 is connected integrally with the proximal member 70 so that the intraocular lens 100 placed on the lens placement portion of the proximal member 70 may be placed in the inside of the tapered distal member 71.

The slider 67 and the plunger 68 are provided so as to be movable back-and-forth in the main body 66. The locking mechanism 69 can limit the forward movement of the plunger 68. The locking mechanism 69 is unlocked by moving the slider 67 forward, thereby allowing the plunger 68 to be movable forward.

The intraocular lens insertion device 61 thus structured allows the intraocular lens 100 to be pushed by the slider 67 so that it is properly folded in a predetermined shape at first, and then allows the intraocular lens 100 to be inserted into an eye by folding the intraocular lens 100 even smaller by continuously pushing the intraocular lens 100 by the plunger 68. Accordingly, the intraocular lens insertion device 61 is structured such that the locking mechanism 69 thereof ensures that the intraocular lens 100 is prevented from being pushed out by the plunger 68 prior to being pushed out by the slider 67, and thus the intraocular lens 100 placed in the main body 66 is folded as it is moved forward in two steps by the slider 67 and then by the plunger.

These matters have already been disclosed by the present applicant. For details relating to the matters, one may refer to the description in Best Mode for Carrying Out the Invention in PCT/JP2008/59995, for example.

In this case, the cylindrical insertion portion according to claim 1 comprises the lens placement portion and the tapered distal member 71, and in the tapered distal member 71, a protrusion insertion hole 73 is drilled so as to penetrate the thickness of the tapered distal member 71 toward the vertical direction z perpendicular to both the lens-advancing direction x and the lateral direction y. According to this embodiment, the protrusion insertion hole 73 is drilled in the approximate center of the lens placement portion 54 so as to cross the lens-advancing axis A, and a hole region is formed in the middle of the transition space in which the intraocular lens 100 moves.

Figure 10:
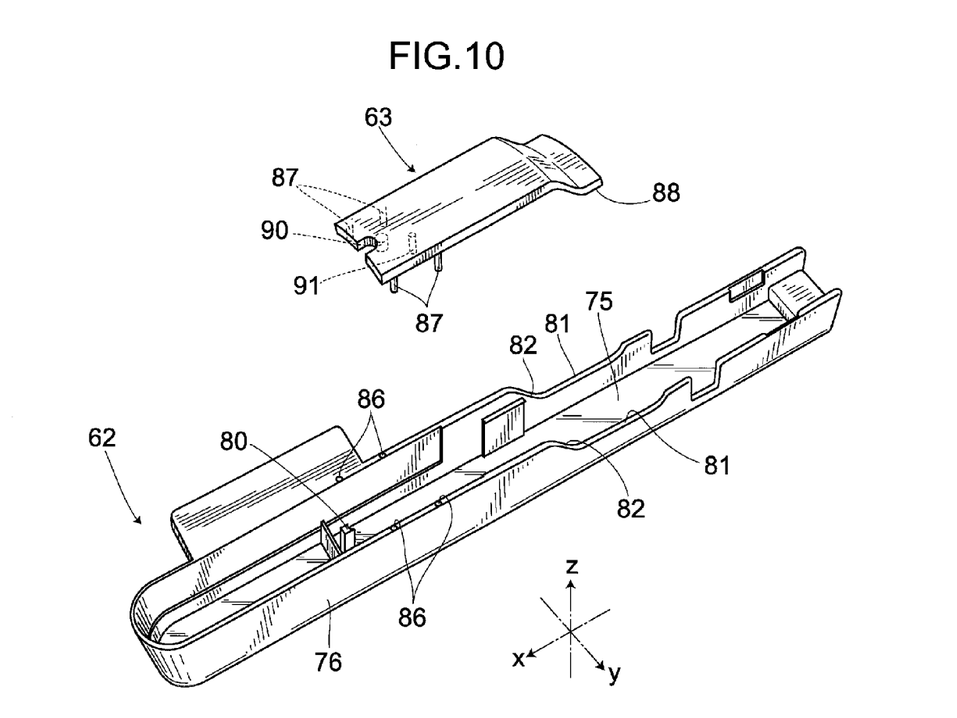
FIG. 10 is a perspective view showing the structures of the casing and a cover body.

The intraocular lens insertion device 61 is capable of being removably attached to the casing 62 which is separate from the intraocular lens insertion device 61 and is formed from e.g., a synthetic resin material into a one-piece structure. As shown in FIG. 10, a U-shaped wall portion 76 is vertically provided on a base plate 75 of the casing 63, in a manner surrounding the intraocular lens insertion device 61, while a protrusion 80 is vertically provided on a given position of the base plate 75.

Figure 11:
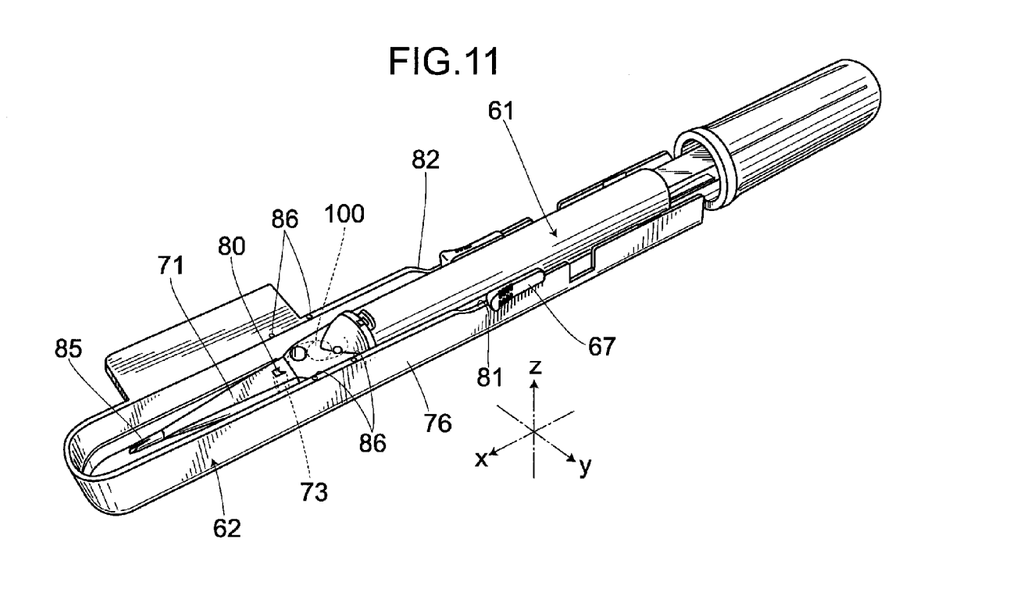
FIG. 11 is a perspective view showing the intraocular lens insertion device placed onto the casing according to the third embodiment.

The protrusion 80 has the same structure as that of the foregoing second embodiment so that it may be, as shown in FIG. 11, inserted into the protrusion insertion hole 73 of the intraocular lens insertion device 61 by installing the intraocular lens insertion device 61 in the casing 62. In this way, in the intraocular lens insertion device 61, the protrusion 80 of the casing 62 can be arranged in the center region of the transition space of the tapered distal member 71.

Also, as shown in FIG. 10, the wall portion 76 of the casing 62 is formed, on its both sides, with a stepped portion 81 whose height from the base plate 75 is comparatively low. As shown in FIG. 11, when the intraocular lens insertion device 61 is installed, the slider 67 of the intraocular lens insertion device 61 is capable of being located on the stepped portion 81.

At this time, there is a given distance between an abutting surface 82 of the wall portion 76 and the slider 67 of the intraocular lens insertion device 61.

Thus, the intraocular lens insertion device 61 can move the intraocular lens 100 installed inside the tapered distal member 71 toward the lens-advancing direction x up to a given position, by allowing the slider 67 in the lens-advancing direction x until it abuts on the abutting surface 82 of the wall portion 76 of the casing 62.

In this way, like in the foregoing second embodiment, the intraocular lens 100 is allowed to have its supporting portion 102 abutted on the protrusion 80 so as to have the tip end of the supporting portion 102 folded back along a curved surface of the protrusion 80 in the backward direction opposed to the lens-advancing direction x. Thus, the intraocular lens insertion device 61 is capable of placing the intraocular lens 100 on the lens placement portion (not shown) with the supporting portion 102 folded in a substantially U-shape by the protrusion 80.

Also, the intraocular lens insertion device 61 is detached from the casing 62 with the above arrangement being retained, and then the intraocular lens 100 is pushed out by the plunger 68 in the lens-advancing direction x with the supporting portion 102 folded back, thereby allowing the intraocular lens 100 to be released from a nozzle 85 of the tapered distal member 71.

In the meantime, as shown in FIG. 10, fitting holes 86 are drilled on the top surface of the wall portion 76 of the casing 62 so that fitting protrusions 87 provided on the lower surface of the cover body 63 may be fitted into the fitting holes 86, thereby allowing the cover body 63 to be attached to the casing 62.

In practice, the contour of the lower surface of the cover body 63 is formed corresponding to that of the top surface of the wall portion 76 of the casing 62, and thus it includes a stepped abutting portion 88 formed corresponding to the shape of the stepped portion 81 of the wall portion 76.

Accordingly, as shown in FIG. 8, when the cover body 63 is attached to the casing 62 on which the intraocular lens insertion device 61 is installed, the stepped abutting portion 88 is fitted in a gap formed between the abutting surface 82 of the wall portion 76 of the casing 62 and the slider 67 of the intraocular lens insertion device 61, thereby preventing the slider 67 from sliding.

Additionally, as shown in FIG. 10, the cover body 63 may have, for example, two positioning protrusions 90, 91 on the lower surface thereof so that the positioning protrusions 90, 91 may be inserted into positioning holes 92, 93 drilled in the tapered distal member 71 of the intraocular lens insertion device 61 (see FIG. 9). Accordingly, when the cover body 63 is attached to the casing 62, the positioning protrusions 90, 91 of the cover body 63 are inserted into these positioning holes 92, 93 respectively, thereby allowing the two supporting portions 102, 102 of the intraocular lens 100 to be properly positioned by allowing them to abut on the positioning protrusions 90, 91. Here, it is to be noted that the intraocular lens insertion device 61 allows a viscoelastic material such as a hyaluronic acid preparation for ophthalmic application to be filled thereinside through one positioning hole 91 by a syringe or the like not shown in the drawings.

From the above-mentioned structure, the intraocular lens insertion device 61 enables the supporting portion 102 of the intraocular lens 100 arranged on the lens-advancing side with respect to the lens-advancing direction x to be bent by the protrusion 80 in the backward direction, thus enabling the curved portion of the supporting portion 102, which has become U-shaped and hardly movable, to be released first when releasing the intraocular lens 100 from the tapered distal member 71, thereby enabling the intraocular lens 100 to be inserted into an eye more easily and stably compared to by the conventional ones.

Other Embodiments

The present invention is not limited to the foregoing embodiments and various modifications are possible within the scope of the gist of the present invention. For example, the protrusion may be formed in a circular or various other shapes. Further, the present invention is also applicable to other intraocular lens which has only one supporting portion, or three, four or more supporting portions provided on the optical portion.

Whilst the supporting portion 102 is folded in a U-shape by the protrusions 21, 52, 80 in the foregoing embodiments, the present invention is not limited thereto, but the supporting portion 102 may be folded in V-, C-, L- or various other shapes by the protrusions 21, 52, 80.

Moreover, whilst the protrusions 21, 52, 80 extending in the vertical direction z are proposed in the foregoing embodiments, the present invention is not limited thereto. Any other protrusions extending in the lateral direction y, oblique direction, or various other directions may be possible, as long as the distal end of the supporting portion 102 of the intraocular lens 100 can be folded in the backward direction which is opposed to the lens-advancing direction x. In these cases, a protrusion insertion hole may be drilled in the cartridge 2, 50 and the tapered distal member 71, corresponding to the extending direction of the protrusion.

Additionally, whilst the protrusions 21, 80 are provided on the casings 22, 62 respectively in the foregoing embodiments, the present invention is not limited thereto, but various other configurations are applicable, such that only the protrusion may be detachably provided, or the protrusion may be provided on the cartridge or tapered distal member itself, and then moved by a slide mechanism.

In addition, whilst the protrusion insertion hole 20 is provided in the vicinity of the lens placement portion 11 in the foregoing embodiments, the present invention is not limited to this. The protrusion 21 may be provided on the lens insertion opening 10, transition portion 12, or various other portions, as long as the tip end of the supporting portion 102 of the intraocular lens 100 can be folded in the backward direction as opposed to the lens-advancing direction x when the intraocular lens is released from the nozzle 13.

In addition to the foregoing, whilst the protrusion insertion hole 20 is drilled through between the top surface and the lower surface of the lens placement portion 11 and the tip of the protrusion 21 is exposed from the top surface of the lens placement portion 11 in the foregoing embodiments, the present invention is not limited thereto. The protrusion insertion hole 20 may be drilled through only the lower surface of the lens placement portion 11 so that the tip of the protrusion 21 may not be exposed from the top surface of the lens placement portion 11.

The invention claimed is:

1. An apparatus for use with an intraocular lens including an optical portion and support portions, the apparatus comprising:
   an intraocular lens cartridge defining an outer surface and including a lens placement portion, a nozzle that is configured to be inserted into an eye, an internal lumen that extends from the lens placement portion to the nozzle and through which the intraocular lens passes in a lens advancement direction, a lens insertion opening through which the intraocular lens passes into the lens placement portion while moving in the lens advancement direction, and an aperture that extends from the outer surface to the internal lumen; and
   a cartridge case including a main body, that is configured to be removably attached to the intraocular lens cartridge, and a protrusion;
   wherein the intraocular lens cartridge and the cartridge case are respectively configured such that, when the cartridge case is attached to the intraocular lens cartridge while the entire intraocular lens optical portion is outside the intraocular lens cartridge, the protrusion extends through the aperture and into the internal lumen and the intraocular lens optical portion is movable relative to the protrusion in the lens advancement direction into the intraocular lens cartridge through the insertion opening.

2. An apparatus as claimed in claim 1, wherein the aperture is located between the lens placement portion and the nozzle.

3. An apparatus as claimed in claim 1, wherein
   the intraocular lens cartridge includes a transition portion between the lens placement portion and the nozzle;
   the internal lumen is tapered within the transition portion; and
   the aperture is located within the tapered transition portion.

4. An apparatus as claimed in claim 1, wherein
   the intraocular lens cartridge includes insertion grooves that respectively extend from the outer surface to the internal lumen and from the insertion opening to a groove end; and
   the aperture is located between the insertion groove ends and the nozzle.

5. An apparatus as claimed in claim 4, wherein
   the internal lumen defines a lens-advancing axis and a circumference that extends around the lens-advancing axis;
   the aperture is circumferentially offset from the insertion grooves.

6. An apparatus, comprising:
   an intraocular lens insertion device defining an outer surface and including a lens placement portion, a nozzle that is configured to be inserted into an eye, an internal lumen that extends from the lens placement portion to the nozzle and through which the intraocular lens passes, a plunger configured to push the intraocular lens through the nozzle, and an aperture that extends from the outer surface to the internal lumen;
   an intraocular lens, including an optical portion and first and second support portions, stored in the lens placement portion in a substantially unstressed state with the first support portion between the nozzle and the optical portion; and
   an insertion device case including a main body with a distal end, that is configured to be removably attached to the insertion device, and a protrusion;
   wherein the insertion device and the insertion device case are respectively configured such that the protrusion extends through the aperture and into the internal lumen through which the intraocular lens passes at a location between the nozzle and the first support portion, and the distal end of the case is located distal of the nozzle, when the insertion device case is attached to the insertion device.

7. An apparatus as claimed in claim 6, wherein the aperture is located between the lens placement portion and the nozzle.

8. An apparatus as claimed in claim 6, wherein
   the insertion device includes a transition portion between the lens placement portion and the nozzle;
   the internal lumen is tapered within the transition portion; and
   the aperture is located within the tapered transition portion.

9. An apparatus as claimed in claim 6, wherein
   the insertion device includes a proximal member and a distal member; and
   the aperture extends through the distal member.

10. An apparatus as claimed in claim 6, wherein the insertion device includes a slider that is movable relative to the plunger.

\* \* \* \* \*